United States Patent [19]

Riitano et al.

[11] 4,231,738
[45] Nov. 4, 1980

[54] CANAL INSTRUMENT FOR ELIMINATING INTERFERENCE, WIDENING THE OPENING AND THE CONTEMPORANEOUS FLARED REAMING OF THE FIRST TWO-THIRDS OF THE DENTAL RADICULAR CANALS

[76] Inventors: Francesco Riitano, Corso Umberto 1°(Palazzo Tiani), Soverato (Catanzaro); Vincenzo Spina, Via Fogliano 35, Rome, both of Italy

[21] Appl. No.: 859,077

[22] Filed: Dec. 9, 1977

[30] Foreign Application Priority Data

Dec. 9, 1976 [IT] Italy .................................. 3607 A/76

[51] Int. Cl.$^2$ .............................................. A61C 5/02
[52] U.S. Cl. .................................................. 433/102
[58] Field of Search .................. 32/57, 48, 59, 58, 50, 32/40 R; 15/104.1 C, 104.02, 104.16, 104 SN, 104.05; 128/304, 52; 408/714; 407/12, 13; 29/78, 76; 175/385, 389; 131/243, 245, 246; 145/114

[56] References Cited

U.S. PATENT DOCUMENTS

| | | | |
|---|---|---|---|
| 1,499,970 | 7/1924 | Bush | 32/57 |
| 2,318,696 | 5/1943 | Linden | 15/104.05 |
| 2,503,380 | 4/1950 | Derby | 15/104.05 |
| 2,701,559 | 2/1955 | Cooper | 15/104 SN |
| 3,781,996 | 1/1974 | Saffro | 32/57 |
| 3,884,239 | 5/1975 | Bucalo | 15/104.16 |
| 4,028,810 | 6/1977 | Vice | 32/57 |

FOREIGN PATENT DOCUMENTS 2274267 6/1975 France .................................. 433/102

OTHER PUBLICATIONS

"Retail Price List of A. S. Koch & Sons," Oct. 9, 1929, Lancaster, Pa.

*Primary Examiner*—Louis G. Mancene
*Assistant Examiner*—Michael J. Foycik, Jr.
*Attorney, Agent, or Firm*—Browdy and Neimark

[57] ABSTRACT

Disclosed herein is a canal instrument for eliminating interference and achieving the widening of the opening and the contemporaneous flared reaming of the first two-thirds of the dental radicular canals, the instrument being designed in such a way that over the full length it progressively reduces in thickness towards the tip, while the cutting part that extends from the terminal part or the instrument coupling section to an endodontic drill only extends for a part of the working length.

2 Claims, 19 Drawing Figures

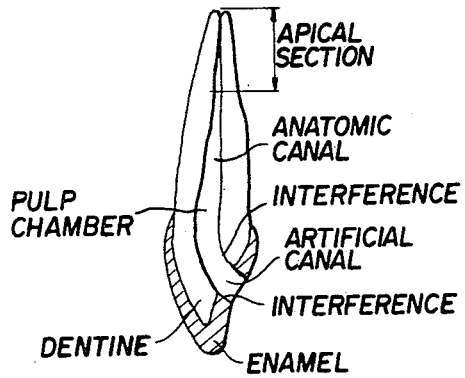
FIG.1 TOP CANINE
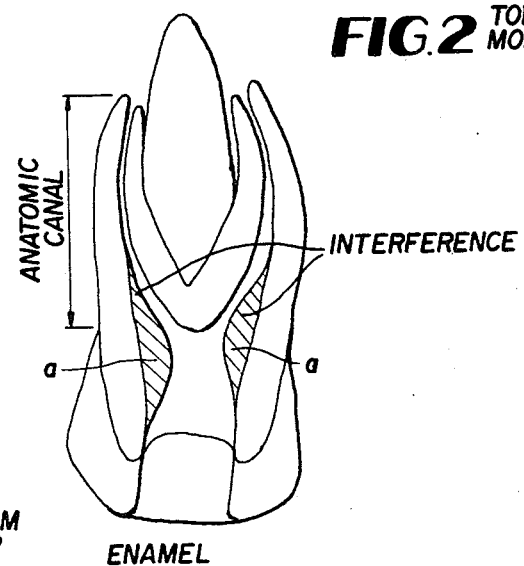
FIG.2 TOP MOLAR
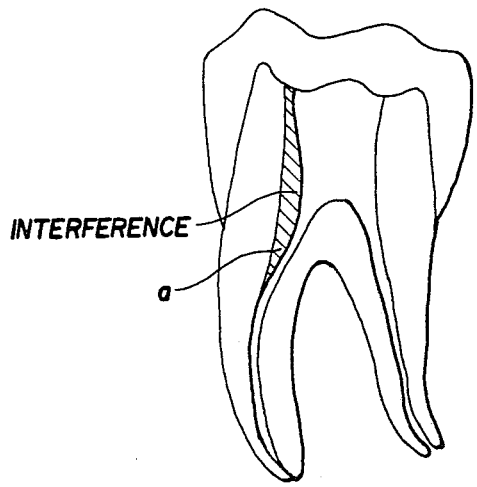
FIG.3 BOTTOM MOLAR
FIG.4 BATT BURR
PRIOR ART
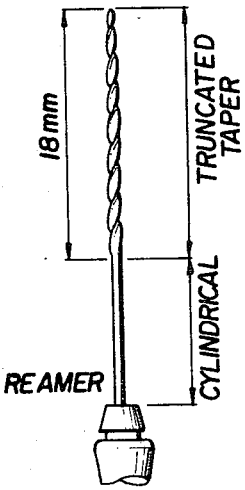
FIG.5 PRIOR ART
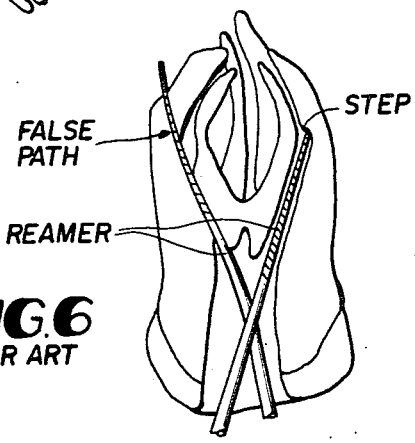
FIG.6 PRIOR ART

APICAL FLARE
REAMER

STEPS

CYLINDRICAL  HEDSTROEM
18 mm a, WIDENER
b, LARGO
c, GATE
d, MAILLEFRER

SD    SD
a
D
S

E
SD

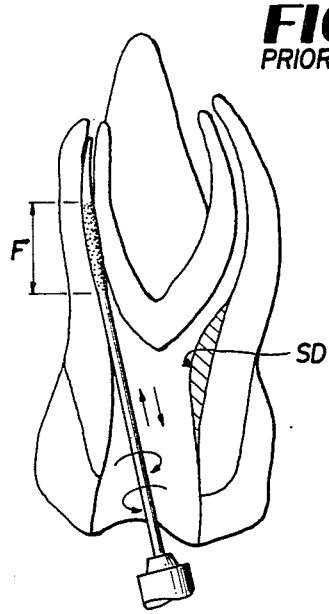
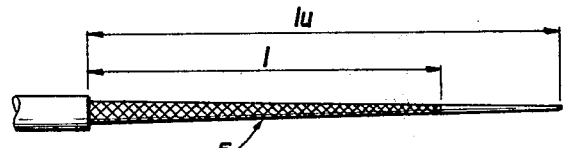
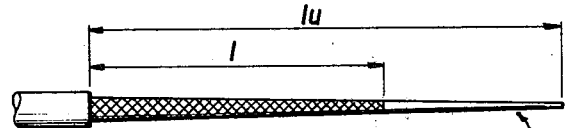
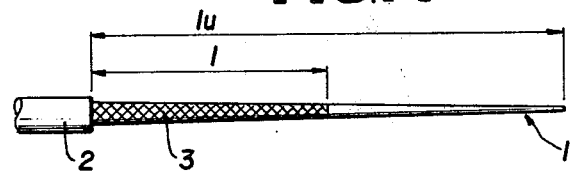
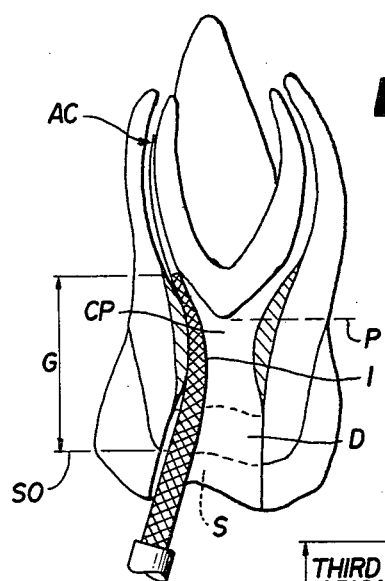
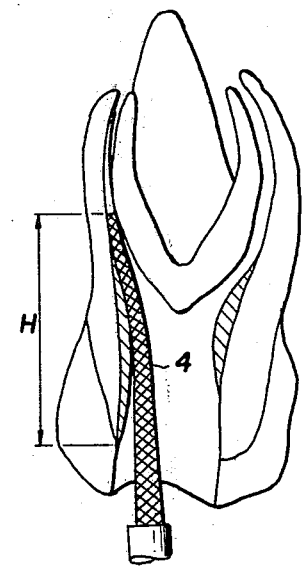
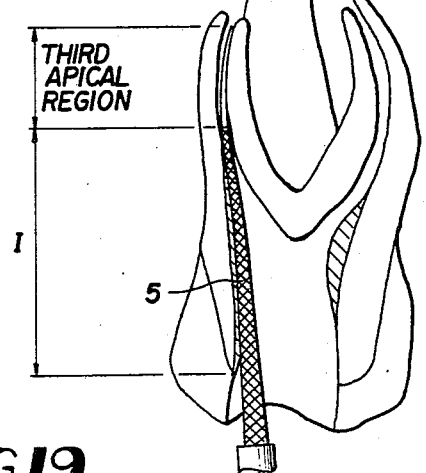

CANAL INSTRUMENT FOR ELIMINATING INTERFERENCE, WIDENING THE OPENING AND THE CONTEMPORANEOUS FLARED REAMING OF THE FIRST TWO-THIRDS OF THE DENTAL RADICULAR CANALS

BACKGROUND OF THE INVENTION

This invention relates to endodontia which is specifically the practice of emptying dental radicular canals using instruments, manual or actuated by mechanical means, commonly known as "endodontic drills". The subject of the invention is a canal instrument created to contemporaneously:

eliminate cavity interference;
widen the canal openings;
straighten the curved areas of the canal through gradually extended flared reaming, starting from the external occlusion orifice of the "operation canal" and continuing to the third apical region.

In order to clarify the original aspects of the invention in question, it should be understood that:

(1) the term "operation canal" is meant to imply the sum of the anatomic radicular canal and of the artificial canal which makes it possible to penetrate the occlusion surface in the former. This is achieved artificially, through reaming, in the roof of the pulp chamber composed of enamel covered dentine (see FIGS. 1 and 2).

(2) "interference" means all anatomic formations characteristic of the walls of the pulp chamber and of the radicular canals which, in the form of crowns, burr or curves, impede the insertion and rectilineal progress of an instrument in the radicular canal, consequently conditioning the work of the reaming surfaces, the stem and the tip of the canal instrument (see FIGS. 1 and 2).

(3) in the majority of cases, the radicular canals have curves which affect them over their full length (as is the case in respect of the mesial canals of the bottom molars (FIG. 3), the vestibular canals of the top molars (FIG. 2) and frequently of the third apical region.

Consequently, the opening of the canals often does not coincide with the axis of the curved section of the canal and, furthermore, is covered with burr formed by the cavity walls at the point where these continue with the floor of the pulp chamber, and thus suitable instruments such as, for example, Batt burrs (see FIG. 4) have to be used to remove at least the upper half of the triangle marked (a) shown in FIGS. 2 and 3 given as examples.

DESCRIPTION OF THE PRIOR ART

Commonly, therefore, only after the pulp chamber has been opened up correctly and the interference of the cavity walls has been overcome, can one get ready to ream the canals. The canal can be of the wide or of the narrow type. Without making any difference in one or the other case, the current reaming procedure is based on the use, in an orderly succession, of a number of instruments of growing diameter, commencing with the one that is the most slender which is able to pass right through the canal and arrive at the apex; this radiographed indicates the length of the canal. The instrument being used is replaced from time to time with another of a greater diameter, special "sinking stops" always being first positioned on the stem of the reaming instrument with the intention of achieving full reaming of the canal.

This often cannot be implemented because of the considerable difference between the truncated taper of the instruments and that of the canal, and because of problems emanating from the confusion resulting from various techniques.

The present reaming instruments have, in fact, a 16 mm reaming surface at the tip and a standard truncated taper, and thus on account of the variation in the diameter-length ratio of the radicular canals it is impossible to achieve with these instruments uniform reaming of all the walls of the canal; this condition renders insufficient the removal of impurities and, in consequence, the air tightness of the radicular obturation.

In fact, the organic residues left in the canal are subjected to retraction and this recreates undesired spaces.

When using the reamer instruments shown in FIG. 5, the following can occur:

(A) in narrow and curved canals the reaming operation is difficult, risky and conditioned by the narrowness of the opening, the friction that the reaming part of the thin instruments encounters over its full extension; then when changing over to instruments of a greater number and diameter in order to widen the canal, the increase in the diameter of the instrument is accompanied by the rigidity of the instrument itself which cannot follow the curvature of the canal satisfactorily; the tip of the instrument forced into the curved canal by the narrow opening can often bring about three very serious problems, that is to say:

(1) a step;
(2) a false path;
(3) apical flaring (see FIGS. 6 and 7).

A step or a false path can definitely compromise the recovery of a gangrenous element since both prevent the subsequent instrument from passing easily through the canal and, thereby, from removing the accumulated matter.

The transformation of the approximately round section of the third apical region into an elliptic section compromises the adherence of the "obturation cone" which being of a circular section fails to match the section of the third apical region.

(B) In the case of wide canals, in order to be able to ream the wall of the canal, particularly in the widest part pointing towards the opening, using the said reamers right the way in, the walls in that part of the apical canal need to be reduced considerably in thickness with the risk of decapitating the apex, especially when a canal has a curved apex.

An alternative and less risky method is that of employing reamers from the apex, the instruments in question being of a greater diameter and of a decreasing penetration potential.

In this way (see FIG. 8) there is, however, the risk of creating inside the canals steps which can impede its being passed through easily.

To avoid the foregoing, the straightening of the curves and the widening of the canals has been arrived at using Hedstroems or "axial" reaming traction files (see FIG. 9).

Once the apex has been reached or once they have been inserted, the said instruments, which are a lot more efficient and a lot less dangerous than "reamers", are pulled towards the outside along the walls of the canal in different mesial, distal, lingual-palatine and vestibular directions and this results in a gradual straightening of the curves and a widening of the canal.

In actual practice, however, the said operations are in vain because the said instruments have difficulty in penetrating a rough and uneven surface where there is a high risk of a fracture connected with imprudent torsion maneuvers which the said instruments have difficulty in withstanding, particularly when in curved, thin canals.

Even when used cautiously, avoiding violent torsion, to ream with the said instruments, as they are currently produced, takes a big amount of time and imposes reaming limitations because of the smooth tang past the 16 mm limit of the reaming surface.

In all cases, irrespective of the drilling method and the traditional instruments used, it has been felt opportune and useful to widen the opening of the canal, especially when this is narrow, prior to reaming it. Many instruments have been created for this purpose, and among these the best known are the: Widener, Largo, Gate and Maillefer (see FIGS. 10-a-b-c-d). The said instruments suffer from very considerable limitations because of the rigidity of their stems which absolutely limits non-rectilineal penetration on account of interference.

The diametrical dimension of the reaming structure, which is always large compared with the slenderness of the very tiny, smooth, rigid, tip that has to operate the cut, still remains even with a flexible stem.

The cutting ability of the said instruments is considerable and thus a big risk is run in reaming canals of ribbon, oval or kidney shape since it is possible to go on reducing their thickness until the walls of the said canals or their bifurcations collapse.

The working direction of these instruments continues to be entrusted solely to the skill of the operator due, as stated previously, to the absence of a suitable guide to orientate the widening-opening instrument so that it operates on the axis of the canal, as well as to the rigidity of the stem which results in widening in wrong directions occurring, this being accentuated in areas which ought not be subjected to the reaming action of this instrument (in the polyradicular bifurcation zone, for example).

In order to overcome the foregoing, in another patent application (French patent application publication No. 2,274,267) the same applicants as herein disclosed an instrument whose structure is such as to allow both the anatomic widening of the opening of the canal and its reaming to be performed up to the third apical region in a guided, progressive, manner without any danger of steps or false paths being created.

Starting from its tip, the said instrument comprises: a first extremely flexible part devoid of cutting members; a second, also flexible, part immediately after the first part, this being provided with cutting members; and a third part immediately after the second part, forming the stem of the instrument.

With the said instrument having a smooth and slender tip capable of easily penetrating even curved canals, the reaming of walls is performed with its lateral surface, from the opening towards the apex, through light to-and-fro axial movements given to the instrument, this preferably being mounted on a mechanical device able to transmit a right-left quarter turn torsion motion.

The widening of the opening of the canal, together with the straightening of its curves, is achieved through a guided reaming-widening method with the lateral reaming surface of the instrument being taken to meet each individual section of the canal wall and of the area of interference.

In the past a canal instrument equipped with a smooth guide tip was known and this was described in U.S. Pat. No. 1,499,970 in the name of Bush. With the said instrument it was, however, absolutely not possible to achieve the straightening of any curves in the canal, and it was impossible, in addition, to effect a gradual flared reaming of the canal since it was provided with a head operating reaming structure such, therefore, as to cause the instrument to perform a reaming perforation in order to widen the canal.

According to what was envisaged by the applicants in the aforementioned French Pat. No. 2,274,267, once the opening of the pulp chamber has been effected (see FIGS. 11, 12 and 13 on the accompanying drawings) by removing the enamel (S) and the dentine (D) above the said pulp chamber, using suitable widening-opening instruments to eliminate part of the burr (SD) impeding entry to the canal (utilizing, for example, as already mentioned, Batt burrs), a number of instruments of the type described are used in orderly succession, these having the cutting part gradually closer and closer to the tip in order to bring about the progressive guided reaming of the canal and the contemporaneous straightening of the curves in the successive affected areas (E) and (F) of the walls of the canal, from the opening towards the radicular apex.

Although this solves the considerable problems to which prior reference has been made, pertaining to the widening of the opening and to the guided reaming of the wall of the radicular canals up to the third apical region, to use the aforementioned instrument it is always necessary to first eliminate, through, for example, the previously mentioned Batt burrs or widening-opening instruments, at least the part (a) of burr or interference concealing the entry to the canals.

SUMMARY OF THE INVENTION

The object of the present invention is to remedy the aforementioned difficulties and to contemporaneously improve the procedure for widening dental radicular canals, even with respect to what can be achieved with the instrument forming the subject of the cited French Pat. No. 2,274,267 in the name of the applicants herein.

In their study, the applicants considered the following: (a) to eliminate the use of widening-opening instruments once the roof of the cavity has been demolished, (b) which still today precede the canal instruments; in consideration of the canal opening no longer corresponding to the floor P of the pulp chamber (see FIG. 17) as in the technique known to date, but rather to the occlusion area (SO) (see again FIG. 17), to operationally bring the said opening as much as possible in alignment with the apex (AC) of the canal by eliminating cavity interference and contemporaneously by reaming the canal and straightening its curves; and (c) to achieve the said contemporaneous elimination of cavity interference and the widening of the canal with progressive reaming from the opening (considered at point b) towards the apex, taking into account the morphological reality of the radicular canals which are of a regular, approximately round, section only in the third apical region, whereby it is right and, therefore, necessary, to suitably regularize the walls of the canal ahead of the third apical region in order to then be able to work in the said region itself. This is suggested by the consideration that before proceeding downstream, it is more productive and rational to remove obstacles upstream.

Considering the foregoing, the objects mentioned are attained with the canal instrument forming the subject of the present invention, essential features of which are that over the full working length thereof it progressively reduces in thickness towards the tip, while the cutting part which commences at the terminal or coupling part that fits into an endodontic drill, only extends over a section of the working length of the instrument in question.

BRIEF DESCRIPTION OF THE DRAWINGS

FIG. 14 depicts the instrument forming the subject of the invention in one possible form of embodiment;

FIGS. 15 and 16 depict two instruments similar to that illustrated in FIG. 14, with the cutting part more extended towards the tip;

FIGS. 17, 18 and 19 depict three sections of a tooth with the instrument in three successive operating phases.

DESCRIPTION OF THE PREFERRED EMBODIMENT

Figure 7:
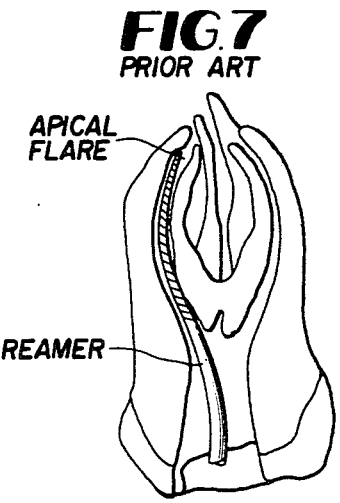
Figure 8:
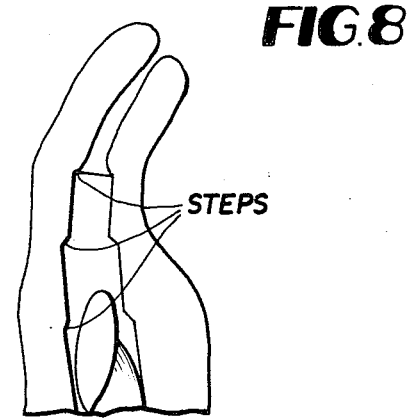
Figure 9:
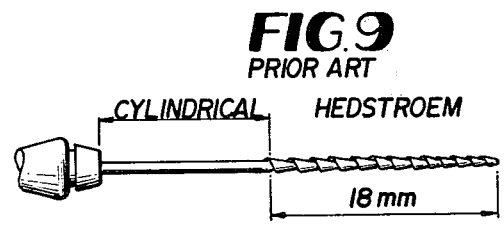
Figure 10:
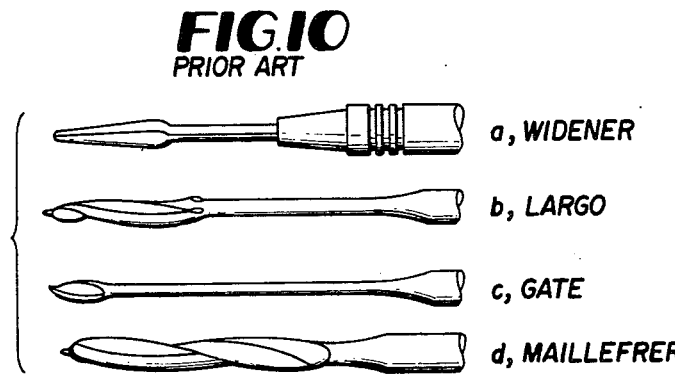
Figure 11:
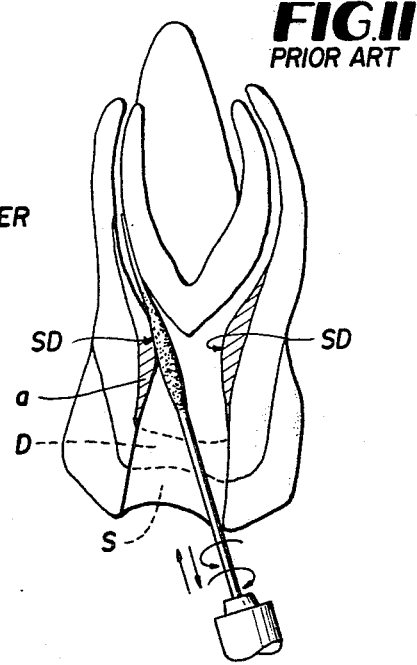
Figure 12:
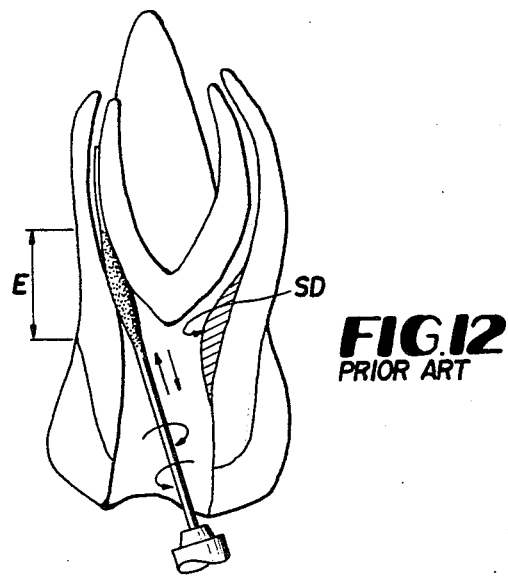

With reference to FIG. 14, the instrument in question, given globally the number (1), which can be made of any suitable material, has in this particular instance a taper over its full working length (lu) which commences at its tip and goes towards the terminal or coupling part (2) that fits into an endodontic drill or into a manually operated drill not illustrated in the drawings.

The said instrument has a cutting part (3) that only extends for a certain distance (l) from the said terminal or coupling part (2) towards the tip, the length of this being predetermined to suit the gradual operating action it is wished, as will be seen hereinafter, to achieve.

Any suitable technique can be used to create the said cutting part (l). The diameter and the progressive reduction in thickness of the instrument are suitably calculated to give it ever less flexibility from the tip towards the coupling part (2) and to make it possible to use a very restricted number of instruments with which to completely ream all the radicular canals of teeth of different types.

Using a limited number of instruments of the said type having the cutting part "l" ever more extended towards the tip as, for example, instruments (4) and (5) illustrated in FIGS. 15 and 16, it is possible to keep to the operating procedure outlined in FIGS. 17, 18 and 19.

Once, with the use of special instruments, the thickness of the enamel (S) of the tooth and the thickness of the dentine (D) that covers the pulp chamber (CP) has been removed, the operator, using the instrument (1), which due to its flexibility and to its tip not having any cutting parts, can be easily guided in the canal, first eliminates the burr and interference offered by the walls of the pulp chamber concealing the entry to the canal (the said burr or interference is shown in phantom lines in FIG. 17 and is marked (G)), then effects an initial flared reaming of the canal. Subsequently, changing this instrument over for instruments (4) and (5), and thanks to the taper the instrument has been given, the flared reaming action proceeds in fresh areas of the wall of the canal, gradually getting closer and closer to the apex, and this affects at the same time all parts (H) and (I) upstream, as far as the opening considered to correspond to the occlusion section (SO). Because of the fact that the cutting part always extends from the terminal or coupling part towards the tip, the walls of the canal are progressively remodelled, and this includes, as seen previously, the elimination of cavity interference and the straightening of any curves present in the canal.

On account of the characteristics of the instrument, there is always a favorable thrust on the part of this against the wall of the canal opposite the curve in the said canal and thus the whole zone of the canal prior to the third apical region (the deepest part of the canal) is favorably widened with the full elimination of obstacles so as to align the opening with the apex without the canal having areas in which there is a lack of operating continuity and, therefore, without steps or undulations on the walls.

With a set of instruments of the type in question an operating procedure is achieved which can be defined as a gradual flared reaming of the canal from the opening towards the third apical region, and this makes it possible to do away with all the operations for the removal of interference and for the widening of the canal openings currently effected using numerous instruments of various types, following a procedure which is prevalently based on the reaming perforation of the canal.

It is obvious from the foregoing that the instrument according to the invention fully achieves the preset objects.

As already stated, due in fact to its particular structure and especially the fact that the cutting part extending from the terminal or coupling part towards the tip is based on a concept that is quite different from that used for the known instruments, the possibility exists of easily guiding the instrument in the canal without any danger of creating steps on the walls of the canals or of tracing false paths therein and, contemporaneously, of discarding the traditional widening opening instruments and reamers. The latter, however, would still play a part in reaming and remodelling the third apical region which is outside the scope of the instrument in question.

Besides this, full and effective flared reaming of the canal is achieved with the opening of this considered on the level of the occlusion section and not of the floor of the pulp chamber, this going from the said opening towards the apex with optimum straightening and widening of the canal to the advantage of the subsequent canal obturation operations.

The invention is obviously not limited just to the forms of embodiment described and illustrated and thus it is understood that variants of a constructional nature can be introduced, in the same way that, for example, the cutting part could be constructed according to any suitable method, without in any way deviating from the framework of protection for the invention or from the following claims.

What is claimed is

1. A flexible canal instrument for the elimination of interference, the widening of the opening, and the contemporaneous flared reaming of the first two-thirds of the dental radicular canals, the instrument having a tip end and a terminal end distal from said tip end, and having a continuous reduction in diameter over the full working length thereof from said terminal end to said tip end, whereby the instrument becomes continuously more flexible from said terminal end toward said tip end, the instrument further having a cutting part extending from said terminal end toward said tip end for only a part of said working length, thereby leaving a smooth tip portion at the tip end thereof for easy guidance in the canal.

2. A kit comprising a plurality of canal instruments in accordance with claim 1, each having identical dimensions and each instrument of said plurality differing from one another by the fact that the cutting part thereof extends to a different distance along the working length thereof toward said tip than that of the other instruments in the kit.

* * * * *